United States Patent
Choung et al.

(10) Patent No.: US 11,376,233 B2
(45) Date of Patent: Jul. 5, 2022

(54) COMPOSITION, CONTAINING SARPOGRELATE AS ACTIVE INGREDIENT, FOR PREVENTING OR TREATING SENSORINEURAL HEARING LOSS

(71) Applicant: AJOU UNIVERSITY INDUSTRY-ACADEMIC COOPERATION FOUNDATION, Gyeonggi-do (KR)

(72) Inventors: Yun-Hoon Choung, Seoul (KR); Young Sun Kim, Gyeonggi-do (KR); Young-Joon Park, Seoul (KR)

(73) Assignee: AJOU UNIVERSITY INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 256 days.

(21) Appl. No.: 16/604,759

(22) PCT Filed: Apr. 10, 2018

(86) PCT No.: PCT/KR2018/004184
§ 371 (c)(1),
(2) Date: Oct. 11, 2019

(87) PCT Pub. No.: WO2018/190608
PCT Pub. Date: Oct. 18, 2018

(65) Prior Publication Data
US 2020/0121629 A1    Apr. 23, 2020

(30) Foreign Application Priority Data
Apr. 11, 2017 (KR) .................. 10-2017-0046741

(51) Int. Cl.
| | | |
|---|---|---|
| *A61K 31/216* | (2006.01) | |
| *A61P 27/00* | (2006.01) | |
| *A61K 31/05* | (2006.01) | |
| *A61K 36/16* | (2006.01) | |
| *A61K 36/258* | (2006.01) | |
| *A61K 36/87* | (2006.01) | |

(52) U.S. Cl.
CPC ............ *A61K 31/216* (2013.01); *A61K 31/05* (2013.01); *A61K 36/16* (2013.01); *A61K 36/258* (2013.01); *A61K 36/87* (2013.01); *A61P 27/00* (2018.01)

(58) Field of Classification Search
None
See application file for complete search history.

(56) References Cited

U.S. PATENT DOCUMENTS

2017/0095506 A1    4/2017    Miller et al.

FOREIGN PATENT DOCUMENTS

| EP | 0072942 A2 | 2/1983 |
|---|---|---|
| KR | 1020080015620 A | 2/2008 |
| KR | 1020110095194 A | 8/2011 |
| KR | 101612762 B1 | 4/2016 |
| WO | 2013147556 A1 | 3/2013 |
| WO | 2013147556 A1 | 10/2013 |

OTHER PUBLICATIONS

Konig, O et al Hearing Research 2006, vol. 221, pp. 59-64.*
Cho, C. et al Korean J Audiol 2013 vol. 17, pp. 83-89.*
Xenellis. J. et al., Otolaryngol.—Head and Neck Surg. 2006, vol. 134, pp. 940-945.*
Cho, C. et al., Kor. J. Audiol. 2013 vol. 17, pp. 83-89.*
Lee, J.-W. et al., Kor. J. Audiol. 2013 vol. 17, pp. 74-77.*
Cho, C.G., et al., "Evaluation of Anxiety and Depressive Levels in Tinnitus Patients", "Korean J. Audiol", 2013, pp. 83-89, vol. 17.
Lee, K.Y., et al., "Novel Therapy for Hearing Loss: Delivery of Insulin-Like Growth Factor 1 to the Cochlea Using Gelatin Hydrogel", "Otology and Neurotology", 2007, pp. 976-981, vol. 28.
Drouet, L., et al., "Plasma Serotonin is Elevated in Adult Patients with Sudden Sensorineural Hearing Loss", Cellular Haemostasis and Platelets, 2020, p. 10.1055/s-0040-1713924.ISSN 0340-6245., vol. DOI https://doi.org/.
Savastano, M., "Tinnitus with or without hearing loss: are its characteristics different?", Eur Arch Otorhinolaryngol, 2008, pp. 1295-1300, vol. 265.
Schreiber, B.E., et al., "Sudden sensorineural hearing loss", Lancet, 2010, pp. 1203-1211, vol. 375, Publisher: www.thelancet.com.
Cummings Otolaryngology Head and Neck Surgery, Editors: Flint, P.W., et al., 2021, Seventh Edition, Chapters 152-154, Publisher: Elsevier, Inc.

* cited by examiner

Primary Examiner — Heidi Reese
(74) Attorney, Agent, or Firm — Hultquist, PLLC; Steven J. Hultquist

(57) ABSTRACT

The present invention relates to a pharmaceutical composition, containing sarpogrelate or a pharmaceutically acceptable salt thereof as an active ingredient, for preventing, alleviating, or treating sensorineural hearing loss. The sarporgrelate according to the present invention protects against hearing loss caused by noise through the suppression of auditory cell apoptosis and the expression increase of antioxidant enzyme in auditory cells, and thus can be advantageously used in the prevention and alleviation of sensorineural hearing loss.

10 Claims, 3 Drawing Sheets
(3 of 3 Drawing Sheet(s) Filed in Color)

COMPOSITION, CONTAINING SARPOGRELATE AS ACTIVE INGREDIENT, FOR PREVENTING OR TREATING SENSORINEURAL HEARING LOSS

CROSS-REFERENCE TO RELATED APPLICATIONS

This application is a U.S. national phase under the provisions of 35 U.S.C. § 371 of International Patent Application No. PCT/KR18/04184 filed Apr. 10, 2018, which in turn claims priority under 35 U.S.C. § 119 of Korean Patent Application No. 10-2017-0046741 filed Apr. 11, 2017. The disclosures of International Patent Application No. PCT/KR18/04184 and Korean Patent Application No. 10-2017-0046741 are hereby incorporated herein by reference in their respective entireties, for all purposes.

TECHNICAL FIELD

The present invention relates to a composition for preventing, alleviating or treating sensorineural hearing loss containing sarpogrelate or a pharmaceutically acceptable salt thereof as an active ingredient.

BACKGROUND ART

Hearing loss, that is, "deafness", is a very common disease occurring in about 15 to 20% of the population. The percentage of the population suffering from hearing loss is gradually increasing due to environmental pollution and aging in modern society, and it is considerably important to prevent auditory disorders prior to the occurrence thereof because such disorders are permanent. Hearing loss is mainly caused by environmental factors such as suddenness, medications (antibiotics such as aminoglycoside or anticancer drugs), noise, trauma, senility and congenital factor caused by genetic factors, and is often sensorineural hearing loss caused by damage and death of auditory cells.

For the treatment of sensorineural hearing loss, signaling pathway mechanisms involved in the regeneration of inner ear hair cells, and the proliferation and differentiation of hair cells have been actively identified, and, in recent years, research on regeneration of hair cells has rapidly progressed through the development of technologies associated with gene therapy (gene editing) or cell transplantation. However, the development of mechanisms or preventive or therapeutic agents associated with the inhibition and prevention of hearing loss remains unsatisfactory (Hanyang Med Rev, 2015).

With the industrialization of society, recently, the incidence of hearing loss caused by noise has also rapidly increased. In addition to occupational noise-induced hearing loss experienced by workers working in noisy environments, noise-induced hearing loss due to cultural and leisure activities is also increasing. Human auditory organs are reported to be affected by noise of 75 dBA or higher. Noise of 75 dBA corresponds to the level of noise at the side of a road on which cars travel. In industrial society, everyone can be considered to be living in noise that is harmful to auditory organs. In addition to environmental noise, which is inevitably heard, people are often exposed to loud sounds during leisure activities, including the use of MP3 players. Recently, noise-induced hearing loss has appeared in various age groups. Noise-induced hearing loss experienced in youth becomes more severe with aging. That is, as the young generation experiencing noise-induced hearing loss become older, the degree of hearing loss becomes more severe, and hearing loss has a significant effect on the quality of life of various generations, from the elderly to the young.

Attempts to prevent and treat noise-induced hearing loss have mainly focused on antioxidant therapy using antioxidants. In particular, vitamin E, aspirin and N-acetylcysteine have effects of reducing the toxicity of aminoglycoside antibiotics, but potent preventive drugs have not been developed yet. Despite many studies attempting to prevent and treat hearing loss, neither a clear molecular mechanism of hearing loss nor potent methods for preventing and treating the same have been proposed to date.

Sarpogrelate is a platelet aggregation inhibitor having a novel mechanism of action that selectively antagonizes serotonin receptors (5-HT2) in platelets and blood vessels and is one of several agonists that activate platelets. Sarpogrelate is known to be stored in platelets and secreted to activate platelets, and, at the same time, to facilitate vasoconstriction and growth of smooth muscle cells and to thereby block the metabolic process of 5-HT causing thrombus formation and vascular blockage. In addition, it is known that, among various causes of hearing loss, microvascular disorders and vasoconstriction deteriorate the functions of auditory nerves and auditory cells, resulting in hearing loss.

Therefore, as a result of extensive efforts to identify the molecular mechanism of hearing loss induced by noise, and to prevent and treat hearing loss, the present inventors have found that sarpogrelate, which improves microvascular disorders, is capable of alleviating hearing loss and inhibiting deterioration in hearing in noise-induced hearing loss animal models and cell line models. Based on this finding, the present invention has been completed.

DISCLOSURE

Technical Problem

Therefore, the present invention has been made in view of the above problems, and it is one object of the present invention to provide a composition for preventing sensorineural hearing loss, containing sarpogrelate or a pharmaceutically acceptable salt thereof as an active ingredient; a complex (combination) preparation for treating sensorineural hearing loss containing the composition and at least one selected from the group consisting of a Korean red ginseng extract, a *Ginkgo biloba* extract, resveratrol and a European *Vitis vinifera* dry leaf extract as an active ingredient; and a composition containing sarpogrelate or a pharmaceutically acceptable salt thereof as an active ingredient, for co-administering with at least one selected from the group consisting of a Korean red ginseng extract, a *Ginkgo biloba* extract, resveratrol and a European *Vitis vinifera* dry leaf extract.

It is another object of the present invention to provide a method of treating sensorineural hearing loss comprising administering a composition containing sarpogrelate or a pharmaceutically acceptable salt thereof; a complex preparation containing the composition and at least one selected from the group consisting of a Korean red ginseng extract, a *Ginkgo biloba* extract, resveratrol and a European *Vitis vinifera* dry leaf extract; and a composition containing sarpogrelate or a pharmaceutically acceptable salt thereof, for co-administering with at least one selected from the group consisting of a Korean red ginseng extract, a *Ginkgo biloba* extract, resveratrol and a European *Vitis vinifera* dry leaf extract.

It is another object of the present invention to provide a use of a composition containing sarpogrelate or a pharmaceutically acceptable salt thereof as an active ingredient; a complex preparation containing the composition and at least one selected from the group consisting of a Korean red ginseng extract, a *Ginkgo biloba* extract, resveratrol and a European *Vitis vinifera* dry leaf extract as an active ingredient; and a composition containing sarpogrelate or a pharmaceutically acceptable salt thereof as an active ingredient, for co-administering with at least one selected from the group consisting of a Korean red ginseng extract, a *Ginkgo biloba* extract, resveratrol and a European *Vitis vinifera* dry leaf extract, for preventing sensorineural hearing loss.

It is another object of the present invention to provide a use of a composition containing sarpogrelate or a pharmaceutically acceptable salt thereof as an active ingredient; a complex preparation containing the composition and at least one selected from the group consisting of a Korean red ginseng extract, a *Ginkgo biloba* extract, resveratrol and a European *Vitis vinifera* dry leaf extract as an active ingredient; and a composition containing sarpogrelate or a pharmaceutically acceptable salt thereof as an active ingredient, for co-administering with at least one selected from the group consisting of a Korean red ginseng extract, a *Ginkgo biloba* extract, resveratrol and a European *Vitis vinifera* dry leaf extract, for the preparation of a medicament for preventing sensorineural hearing loss.

Technical Solution

In accordance with one aspect of the present invention, the above and other objects can be accomplished by the provision of a pharmaceutical composition for preventing or treating sensorineural hearing loss, containing sarpogrelate or a pharmaceutically acceptable salt thereof as an active ingredient.

In accordance with another aspect of the present invention, there is provided a complex preparation for treating sensorineural hearing loss, containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient.

In accordance with another aspect of the present invention, there is provided a composition containing sarpogrelate or a pharmaceutically acceptable salt thereof as an active ingredient, for co-administering with at least one selected from the group consisting of a Korean red ginseng extract, a *Ginkgo biloba* extract, resveratrol and a European *Vitis vinifera* dry leaf extract.

In accordance with another aspect of the present invention, there is provided a food composition for preventing or alleviating sensorineural hearing loss, containing sarpogrelate or a food acceptable salt thereof as an active ingredient.

In accordance with another aspect of the present invention, there is provided a method of preventing or treating sensorineural hearing loss comprising administering a pharmaceutical composition containing sarpogrelate or a pharmaceutically acceptable salt thereof as an active ingredient.

In accordance with another aspect of the present invention, there is provided a method of treating sensorineural hearing loss comprising administering a complex preparation containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient.

In accordance with another aspect of the present invention, there is provided a method of treating sensorineural hearing loss comprising co-administering a composition containing sarpogrelate or a pharmaceutically acceptable salt thereof as an active ingredient with at least one selected from the group consisting of a Korean red ginseng extract, a *Ginkgo biloba* extract, resveratrol and a European *Vitis vinifera* dry leaf extract.

In accordance with another aspect of the present invention, there is provided a use of a pharmaceutical composition containing sarpogrelate or a pharmaceutically acceptable salt thereof as an active ingredient, for preventing or treating sensorineural hearing loss.

In accordance with another aspect of the present invention, there is provided a use of a complex preparation containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient, for treating sensorineural hearing loss.

In accordance with another aspect of the present invention, there is provided a use of a composition containing sarpogrelate or a pharmaceutically acceptable salt thereof as an active ingredient for co-administering with at least one selected from the group consisting of a Korean red ginseng extract, a *Ginkgo biloba* extract, resveratrol and a European *Vitis vinifera* dry leaf extract, for treating sensorineural hearing loss.

In accordance with another aspect of the present invention, there is provided the use of a pharmaceutical composition containing sarpogrelate or a pharmaceutically acceptable salt thereof as an active ingredient, for the preparation of a medicament for treating sensorineural hearing loss.

In accordance with another aspect of the present invention, there is provided the use of a complex preparation containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient, for the preparation of a medicament for treating sensorineural hearing loss.

In accordance with another aspect of the present invention, there is provided the use of a composition containing sarpogrelate or a pharmaceutically acceptable salt thereof as an active ingredient for co-administering with at least one selected from the group consisting of a Korean red ginseng extract, a *Ginkgo biloba* extract, resveratrol and a European *Vitis vinifera* dry leaf extract, for the preparation of a medicament for treating sensorineural hearing loss.

DESCRIPTION OF DRAWINGS

The patent or application file contains at least one drawing executed in color. Copies of this patent or patent application publication with color drawing(s) will be provided by the Office upon request and payment of the necessary fee.

Figure 4:
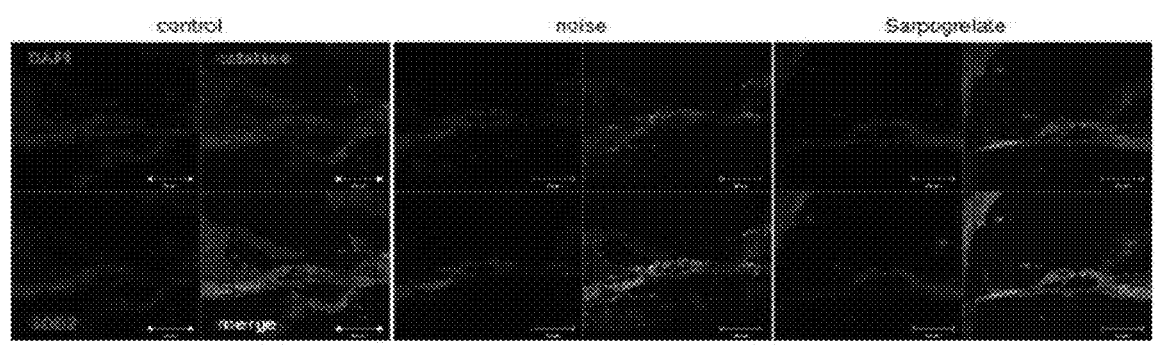
Figure 5:
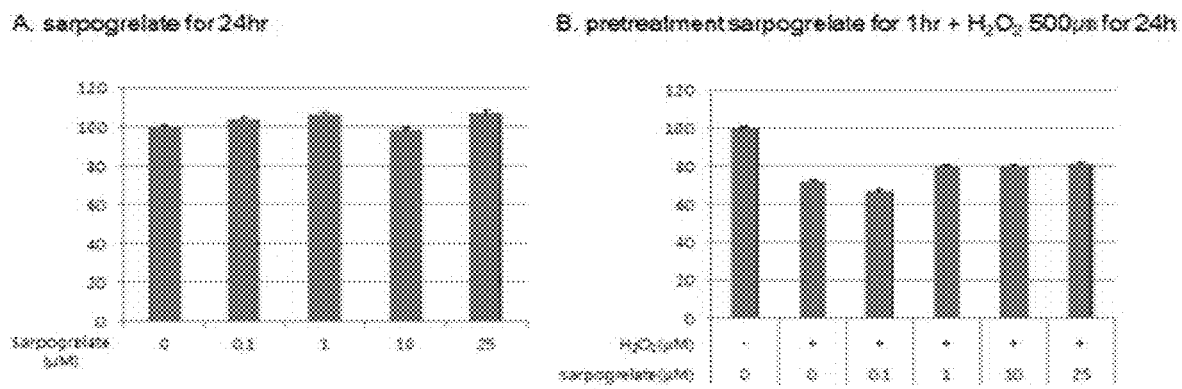
Figure 6:
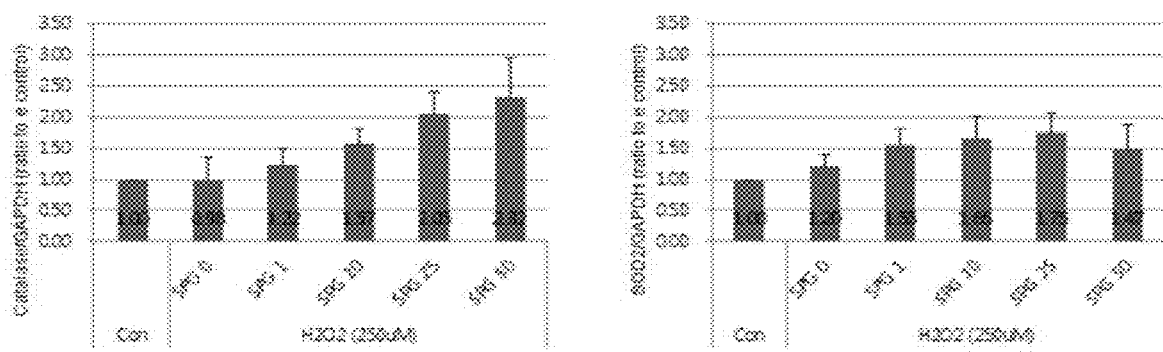
Figure 7:
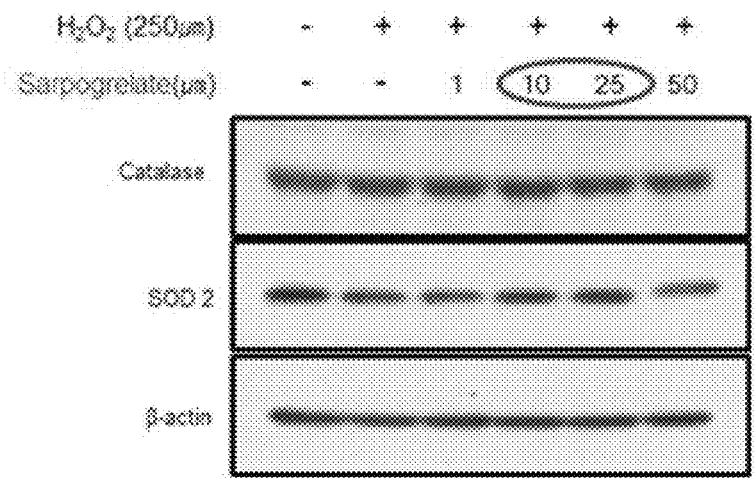

green, SOD2: red, DAPI: blue) in spiral ganglia (apex, middle and base) in the cochlea of mice suffering from noise-induced hearing loss;

FIG. 4 shows the result of evaluation of the effect of sarpogrelate on the expression of antioxidants (catalase: green, SOD2: red, DAPI: blue) in auditory hair cells in the cochlea of mice suffering from noise-induced hearing loss;

FIG. 5 shows the result of WST-1 analysis for evaluating cytotoxicity by $H_2O_2$ treatment and apoptosis after pretreating HEI-OC1 (auditory cell line) cells, with sarpogrelate;

FIG. 6 shows the result of quantitative real-time PCR for evaluating mRNA expression of antioxidants (catalase and SOD2) in auditory cells treated with $H_2O_2$ and sarpogrelate; and FIG. 7 shows the result of Western blotting for evaluating protein expression of antioxidants (catalase and SOD2) in auditory cells treated with $H_2O_2$ and sarpogrelate.

BEST MODE

Unless defined otherwise, all technical and scientific terms used herein have the same meanings as appreciated by those skilled in the field to which the present invention pertains. In general, the nomenclature used herein is well-known in the art and is ordinarily used.

In the present invention, deterioration in hearing loss were found to be inhibited and alleviated through inhibition of apoptosis and expression of intracellular antioxidant enzymes by establishing noise-induced hearing loss mouse models and noise-induced hearing loss cell lines and then treating the same with sarpogrelate. That is, the present invention identifies that sarpogrelate is effective in preventing, alleviating and treating sensorineural hearing loss.

Thus, in one aspect, the present invention is directed to a pharmaceutical composition for preventing or treating sensorineural hearing loss containing sarpogrelate or a pharmaceutically acceptable salt thereof as an active ingredient.

The sarpogrelate of the present invention is represented by the following formula 1, and the IUPAC name thereof is 4-[2-(dimethylamino)-1-({2-[2-(3-methoxyphenyl)ethyl]phenoxy}methyl)ethoxy]-4-oxobutanoic acid.

[Formula 1]

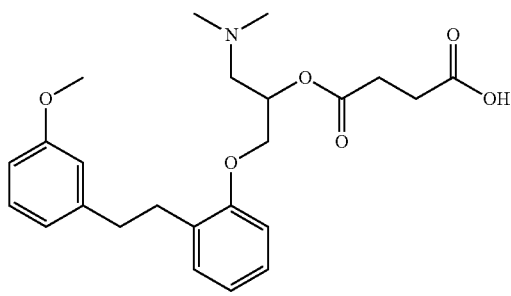

Sarpogrelate exhibits anti-platelet activity and vasoconstriction activity through antagonism specific to serotonin receptors on platelets and vascular smooth muscles. Co-addition of serotonin and collagen to healthy adults and patients suffering from chronic arterial occlusion is identified to cause the inhibitory response to platelet aggregation. Platelet aggregation by collagen and secondary platelet aggregation by ADP or epinephrine are inhibited. Platelet aggregation by collagen is enhanced by serotonin, and such enhanced platelet aggregation is inhibited by sarpogrelate. In addition, sarpogrelate inhibits the onset of the condition in the peripheral arterial occlusion model (rat peripheral arterial occlusion through injection of lauric acid), and has antithrombotic activity to thus inhibit the formation of thrombus in arterial thrombosis models (mouse arterial thrombosis due to vascular endothelial injury, rat arterial thrombosis substituted with polyethylene tube). In-vitro experiments using rat vascular smooth muscles showed that sarpogrelate has activity of inhibiting vascular contraction, including inhibiting the contraction of vascular smooth muscles by serotonin and inhibiting the contraction of vascular smooth muscles accompanied by platelet aggregation.

Therefore, sarpogrelate is commercially available in the form of hydrochloride as a drug for alleviating ischemic symptoms such as ulcers, pain and coldness caused by chronic arterial occlusion (such as Berger's disease, obstructive atherosclerosis, or diabetic peripheral angiopathy). However, to date, no literature has been reported showing a direct relationship between sarpogrelate and hearing loss.

In the present invention, the composition containing sarpogrelate preferably further contains at least one selected from the group consisting of a Korean red ginseng extract, a *Ginkgo biloba* extract, resveratrol and a European *Vitis vinifera* dry leaf extract, but the present invention is not limited thereto.

As used herein, the term "Korean red ginseng" refers to ginseng produced in Korea, and is a representative medicinal plant which is a perennial umbelliferous cotyledon herb that belongs to the Ginseng Family. Preferably, Korean red ginseng means red ginseng obtained as stipulated by the Korean Society of Ginseng, but the present invention is not limited thereto. In addition, Korean red ginseng includes all of fresh ginseng, red ginseng and white ginseng. Ginseng maintaining the original shape of Korean red ginseng is referred to as "main ginseng" and ginseng not maintaining the original shape of Korean red ginseng undergoing processing is referred to "processed ginseng".

The classification of Korean red ginseng is determined depending on the manufacturing method and appearance. Korean red ginseng is classified into red ginseng which is obtained by steaming and drying fresh ginseng, white ginseng which is obtained by drying fresh ginseng, and red and white ginseng products, each of which is obtained by processing fresh ginseng and white ginseng. The Korean red ginseng of the present invention includes all of them, but is not limited thereto.

The red ginseng extract of the present invention may be obtained by extracting with an organic solvent such as water or alcohol as an extraction solvent. Specifically, the red ginseng extract can be obtained using an extraction solvent such as water, aqueous or anhydrous lower alcohol having 1 to 4 carbon atoms, a mixture of the lower alcohol and water, or acetone, ethyl acetate, chloroform, 1,3-butylene glycol, butyl acetate, or the like. Preferably, the red ginseng extract may be prepared using aqueous lower alcohol, most preferably ethanol. The extract of the present invention includes red ginseng extracts having substantially the identical effect prepared using other extraction solvents in addition to the aforementioned extraction solvent.

In addition, the red ginseng extract of the present invention includes not only an extract obtained using the above-described extraction solvent, but also an extract that is subjected to a conventional purification process. For example, the red ginseng extract of the present invention includes active fractions obtained through various additional purification methods such as separation using ultrafiltration membranes having a predetermined molecular weight cut-off value and separation by various kinds of chromatography (manufactured for separation according to size, charge hydrophobicity or affinity). In addition, the red ginseng extract of the present invention may be prepared in the form of a powder through an additional process such as distillation under reduced pressure and freeze drying or spray drying.

The *Ginkgo biloba* extract (GbE) of the present invention is preferably EGb761, but the present invention is not limited thereto. In addition, the ginkgo lateral extract is composed of 24% flavonoid and 6% terpenoid, and is known to be effective in bronchial asthma and bronchitis, peripheral blood disorders, brain dysfunction and the like.

The resveratrol (3,5,4-trans-trihydroxy stilbene) of the present invention is a substance that belongs to polyphenol, which is an antioxidant found in plants, is known to have anti-cancer and antioxidant activities, and is effective in reducing damage to coronary arteries and in preventing blood clotting, which is a dangerous phenomenon that causes heart attacks and strokes. In addition, the European *Vitis vinifera* dry leaf extract of the present invention is also known to contain a lot of antioxidant substances. Resveratrol is more effective than vitamin C in scavenging hydroxyl radicals, and can exert a synergetic effect when used in combination with vitamin A. The use of resveratrol in combination with other antioxidants (excluding vitamin A, C or E, vasodilator magnesium or other vasodilator substances) is known to reduce hearing loss associated with aging.

Among the many causes of hearing loss, smoking and drinking cause microvascular disorders and readily induce hearing loss, and are thus main factors that aggravate chronic diseases, and stress, which causes vasoconstriction, also affects hearing by degrading the functions of auditory nerves and auditory cells. That is, since hearing loss may be caused by microvascular disorders and vasoconstriction, various approaches to preventing hearing-loss-inducing mechanisms using sarpogrelate as a platelet aggregation inhibitor and the development of drugs to prevent noise-induced hearing loss are expected to maximize the quality of life of patients, as well as the therapeutic effects of hearing loss.

Drugs for fundamentally treating hearing loss have not yet been developed to date, and sarpogrelate, as a platelet aggregation inhibitor, can be applied for the prevention and treatment of noise-induced hearing loss by utilizing new drugs to find new indications for drugs currently used in the clinic in order to overcome the considerable time required for the development of new drugs and reduce a clinical trial period. In addition, preventive and therapeutic agents for other hearing loss such as ototoxic hearing loss, sudden hearing loss and age-related hearing loss can be developed by applying the action mechanism of sarpogrelate, and can be used in combination therapy with other treatment methods for hearing loss patients. The action mechanism of sarpogrelate also enables the development of preventive and therapeutic drugs for hearing loss attributable to other causes.

As used herein, the term "sensorineural hearing loss" refers to hearing loss that occurs when the components of the inner ear or accompanying nerve components are affected, and when the auditory cells or auditory nerve pathways of the brain are affected, the nerve or sensory component may be contained. Sensorineural hearing loss may be caused by genetic factors, acoustic trauma (for example, a very loud noise such as an explosion sound), viral infections, drug-induced disease or Meniere's disease. Sensorineural hearing loss may be caused by brain tumors, infections or various brain and neurological disorders such as strokes. Some genetic diseases such as Refsum disease (defective accumulation of branched fatty acids) can also cause neurological diseases that affect hearing loss. Auditory nerve pathways are damaged by demyelinating diseases such as idiopathic inflammatory demyelinating diseases (including multiple sclerosis), transverse myelitis, Devic's disease, progressive multifocal leukoencephalopathy, Guillain-Barré syndrome, chronic inflammatory demyelinating polyneuropathy and anti-MAG peripheral neuropathy.

In the present invention, sensorineural hearing loss is preferably noise-induced hearing loss, ototoxic hearing loss, sudden hearing loss or age-related hearing loss, but the present invention is not limited thereto. In addition, sensorineural hearing loss may be caused by damage to inner ear hair cells and surrounding tissues.

The noise-induced hearing loss of the present invention can be also caused even by exposure to loud noises for long periods of time, such as loud music, heavy equipment or machinery, airplanes, shelling or other human-generated noises. Hearing loss results from the destruction of hair cell receptors in the inner ear. Such hearing loss is often accompanied by tinnitus. Such hearing loss often causes diagnosis with permanent hearing loss. There are no current methods for treating noise-induced hearing loss, but some therapies, including treatment with insulin-like growth factor 1 (IGF-1), are being experimentally developed (Lee et al. *Otol. Neurotol.* 28:976-981, 2007).

The aging-related hearing loss (or senile hearing loss, presbycusis) of the present invention is age-related hearing loss, which occurs as a normal phenomenon of aging, and results from degeneration of receptor cells in the Corti (spiral) organ of the inner ear. Another cause may be a decrease in the number of nerve fibers in the vestibular cochlear nerves as well as loss of flexibility of the basilar membrane of the cochlea. There is currently no known method for treating permanent hearing impairment due to senile hearing loss or excessive noise.

In the present invention, the composition may function to inhibit apoptosis of auditory cells or increase expression of antioxidant enzymes in auditory cells.

As used herein, the term "cochlea" refers to a part of the inner ear associated with hearing. The cochlea is a spiral tubular structure wound like a snail. The interior of the cochlea is divided into three regions, which are distinguished by the location of the vestibular membrane and the basilar membrane. The part above the vestibular membrane is referred to as "scala vestibule", which extends from the oval window to the apex of the cochlea, and contains perilymph, which is an aqueous liquid having low potassium content and high sodium content. The basilar membrane defines "scala tympani", which extend from the apex of the cochlea to the round window, and also contains perilymph. The basilar membrane contains a number of rigid fibers, which gradually increase in length from the garden window to the apex of the cochlea. The fibers of the basilar membrane are vibrated when activated by sound. The cochlear duct is positioned between the scala vestibule and the scala tympani, and the distal end thereof is a closed sac at the apex of the cochlea. The cochlear duct contains endolymph, which is similar to cerebrospinal fluid and has a high potassium content.

The auditory organ known as the "organ of Corti" is located on the basilar membrane and extends upwards to the cochlear duct. The organ of Corti contains hair-like hair cells having protrusions extending from the free surface thereof, and contacts a gelatinous surface called the "tectorial membrane". The hair cells do not have axons, but are surrounded by sensory nerve fibers that form the cochlear branches of vestibulocochlear nerves (brain nerves VIII).

In another aspect, the present invention is directed to a complex preparation for treating sensorineural hearing loss containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient.

In the present invention, the complex preparation is preferably a tablet, an effervescent tablet, a granule, a powder, an injection, a pill or a capsule, but the present invention is not limited thereto.

In formulating two active ingredients into a single formulation, the effects on bioavailability and stability by the physicochemical properties of the two active ingredients, that is, in-vivo and in-vitro interactions between the two active ingredients, should be considered carefully.

In the present invention, the pharmaceutically acceptable salt may include both non-toxic inorganic and organic acid salts, and is preferably, for example, at least one salt selected from the group consisting of hydrochloride, sulfate, mesylate, malate, maleate, mesylate, besylate, hydrogen sulfate, oxalate, fumarate, tartrate, citrate, succinate, acetate and phosphate, and most preferably hydrochloride, but the present invention is not limited thereto.

The sarpogrelate or a pharmaceutically acceptable salt thereof is commercially available or can be easily prepared by a method well-known in the art (European Patent Publication No. 0072942).

In another embodiment of the present invention, the composition containing sarpogrelate or a pharmaceutically acceptable salt thereof may further contain at least one additive selected from the group consisting of additives commonly used for the preparation of compositions including suitable carriers, excipients, disintegrants, sweeteners, coatings, swelling agents, lubricants, slip modifiers, flavors, antioxidants, buffers, bacteriostats, diluents, dispersants, surfactants, binders and lubricants.

Specifically, the carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration may be tablets, pills, powders, granules, capsules and the like, and may be prepared by mixing at least one excipient, for example, starch, calcium carbonate, sucrose, lactose, gelatin or the like. In addition to simple excipients, lubricants such as magnesium stearate and talc are also used. Liquid formulations for oral administration may be suspensions, oral liquids and solutions, emulsions, syrups and the like, and may include various excipients such as wetting agents, sweeteners, fragrances, preservatives and the like, in addition to water and liquid paraffin, which are simple diluents that are commonly used. Formulations for parenteral administration may be sterilized aqueous solutions, non-aqueous solutions, suspensions, emulsions, freeze-dried preparations and suppositories. Examples of non-aqueous solutions and suspensions include propylene glycol, polyethylene glycol, vegetable oil such as olive oil, injectable esters such as ethyl oleate, and the like. Examples of the suppository base include Witepsol, macrogol, Tween 61, cacao butter, laurin butter, glycerogelatin and the like.

The pharmaceutical composition according to the invention may be administered orally (e.g., ingested or inhaled) or parenterally (e.g., by injection, deposition, implantation, suppository), and the injection may be intravenous, subcutaneous, intramuscular or intraperitoneal injection. The pharmaceutical composition according to the present invention may be formulated into tablets, capsules, granules, fine subtilaes, powders, sublingual tablets, suppositories, ointments, injections, emulsions, suspensions, syrups, sprays or the like. The various forms of the pharmaceutical composition according to the present invention can be prepared through a known technique using a pharmaceutically acceptable carrier commonly used in each formulation. Examples of the pharmaceutically acceptable carrier include excipients, binders, disintegrating agents, lubricants, preservatives, antioxidants, isotonic agents, buffers, coating agents, sweeteners, solubilizers, bases, dispersants, wetting agents, suspending agents, stabilizers, coloring agents and the like.

The pharmaceutical composition according to the present invention contains about 0.01 to 95% by weight of the compound of the present invention (sarpogrelate), which depends on the form of the drug.

The dose (used amount) of sarpogrelate, which is an active ingredient of the pharmaceutical composition according to the present invention, may vary depending on the age, gender, body weight and disease of the patient, but is preferably 0.001 to 100 mg/kg, more preferably 0.01 to 10 mg/kg, which may be administered once to several times a day.

In addition, the dosage (administered amount) of sarpogrelate according to the present invention may be increased or decreased depending on the route of administration, disease severity, gender, body weight, age, and the like. Thus, the dosage is not intended to limit the scope of the invention in any aspect.

The pharmaceutical composition may be administered to mammals such as rats, mice, livestock and humans via a variety of routes. All modes of administration may be considered, for example, oral, rectal, intravenous, intramuscular or subcutaneous administration, endotracheal inhalation, or intrauterine dural or intracerebroventricular injection.

As used herein, the term "administration" refers to an action of introducing the pharmaceutical composition according to the present invention into a subject by any appropriate method, and the route of administration of the composition may be any general route, so long as it enables the composition to be delivered to a target tissue.

In another aspect, the present invention is directed to a composition containing sarpogrelate or a pharmaceutically acceptable salt thereof as an active ingredient, for co-administering with at least one selected from the group consisting of a Korean red ginseng extract, a *Ginkgo biloba* extract, resveratrol and a European *Vitis vinifera* dry leaf extract.

In the present invention, conventional respective single preparations are preferably co-administered, and sarpogrelate is freely co-administered with at least one selected from the group consisting of a Korean red ginseng extract, a *Ginkgo biloba* extract, resveratrol and a European *Vitis vinifera* dry leaf extract.

In the present invention, the co-administration is preferably carried out sequentially, simultaneously or in reverse order, but the present invention is not limited thereto.

The composition of the present invention may be administered in a therapeutically effective amount, and the term "therapeutically effective amount" refers to an amount which is sufficient for treating a disease at a reasonable benefit/risk ratio applicable to all medical treatments, and the effective dosage level may vary depending on a variety of factors including severity of the disease, activity of the drug, the age, body weight, health conditions and gender of the patient, sensitivity of the patient to the drug, administration time, administration route and excretion rate of the composition according to the present invention, treatment period, and drugs mixed with the used composition or concurrently used therewith, and other factors well-known in the pharmaceutical field. The pharmaceutical composition of the present invention may be administered as a single therapeutic agent or in combination with other therapeutic agents, and may be administered sequentially or simultaneously with a conventional therapeutic agent. In addition, the pharmaceutical composition may be administered in one or multiple doses. Taking into consideration these factors, it is important to administer the minimum amount sufficient to achieve maximum efficacy without side effects.

In another aspect, the present invention is directed to a method of preventing or treating sensorineural hearing loss comprising administering a pharmaceutical composition containing sarpogrelate or a pharmaceutically acceptable salt thereof as an active ingredient.

In another aspect, the present invention is directed to a method of treating sensorineural hearing loss comprising administering a complex preparation containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient.

In another aspect, the present invention is directed to a method of treating sensorineural hearing loss comprising co-administering a composition containing sarpogrelate or a pharmaceutically acceptable salt thereof as an active ingredient with at least one selected from the group consisting of a Korean red ginseng extract, a *Ginkgo biloba* extract, resveratrol and a European *Vitis vinifera* dry leaf extract.

In another aspect, the present invention is directed to the use of a pharmaceutical composition containing sarpogrelate or a pharmaceutically acceptable salt thereof as an active ingredient, for preventing or treating sensorineural hearing loss.

In another aspect, the present invention is directed to the use of a complex preparation containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient, for preventing or treating sensorineural hearing loss.

In another aspect, the present invention is directed to the use of a composition containing sarpogrelate or a pharmaceutically acceptable salt thereof as an active ingredient for co-administering with at least one selected from the group consisting of a Korean red ginseng extract, a *Ginkgo biloba* extract, resveratrol and a European *Vitis vinifera* dry leaf extract, for treating sensorineural hearing loss.

In another aspect, the present invention is directed to the use of a pharmaceutical composition containing sarpogrelate or a pharmaceutically acceptable salt thereof as an active ingredient, for the preparation of a drug for treating sensorineural hearing loss.

In another aspect, the present invention is directed to the use of a complex preparation containing sarpogrelate or a pharmaceutically acceptable salt thereof and at least one selected from the group consisting of a Korean red ginseng extract, a *Ginkgo biloba* extract, resveratrol and a European *Vitis vinifera* dry leaf extract as an active ingredient, for the preparation of a drug for treating sensorineural hearing loss.

In another aspect, the present invention is directed to the use of a composition containing sarpogrelate or a pharmaceutically acceptable salt thereof as an active ingredient for co-administering with at least one selected from the group consisting of a Korean red ginseng extract, a *Ginkgo biloba* extract, resveratrol and a European *Vitis vinifera* dry leaf extract, for the preparation of a drug for treating sensorineural hearing loss.

In another aspect, the present invention is directed to a food composition for preventing or alleviating sensorineural hearing loss containing sarpogrelate or a food acceptable salt thereof as an active ingredient.

In the present invention, the food composition preferably further contains at least one selected from the group consisting of a Korean red ginseng extract, a *Ginkgo biloba* extract, resveratrol and a European *Vitis vinifera* dry leaf extract, but the present invention is not limited thereto.

In the present invention, sensorineural hearing loss is noise-induced hearing loss, ototoxic hearing loss, sudden hearing loss or age-related hearing loss, but the present invention is not limited thereto. In addition, sensorineural hearing loss may be caused by damage to inner ear hair cells and surrounding tissues.

In the present invention, the food composition preferably further contains a food acceptable additive, but the present invention is not limited thereto.

The food composition may be provided in the form of a powder, granule, tablet, capsule, syrup or beverage. The health food may be used in combination with food or food additives other than sarpogrelate, which is an active ingredient, and can be suitably used in accordance with a conventional method. The amount of the active ingredient to be mixed therewith can be suitably determined according to the use purpose thereof, for example, prevention, health or therapeutic treatment.

The effective dose of the sarpogrelate contained in the food composition may be used in accordance with the effective dose of the pharmaceutical composition. However, in the case of long-term intake for the purpose of health and hygiene or for the purpose of health management, the effective dose may be not more than the range defined above, and it will be obvious that the active ingredient can be used in an amount exceeding the range because there is no problem in terms of safety.

There is no particular limitation as to the kind of the food composition. Examples of the food composition include meat, sausage, bread, chocolate, candy, snacks, confectionery, pizza, ramen, other noodles, gum, dairy products including ice cream, various soups, beverages, tea, drinks, alcoholic beverages, vitamin complexes and the like. The food composition includes all health foods in the conventional sense.

The food composition may include a health beverage composition and may contain additional ingredients such as various flavors or natural carbohydrates, like general beverages. The natural carbohydrates include monosaccharides such as glucose and fructose, disaccharides such as maltose and sucrose, polysaccharides such as dextrin and cyclodextrin, and sugar alcohols such as xylitol, sorbitol and erythritol. As sweeteners, natural sweeteners such as thaumatin and stevia extracts or synthetic sweeteners such as saccharin and aspartame can be used.

EXAMPLE

Hereinafter, the present invention will be described in more detail with reference to examples. However, it will be obvious to those skilled in the art that these examples are provided only for illustration of the present invention and should not be construed as limiting the scope of the present invention based on the subject matter of the present invention.

Example 1

In-Vivo Test Using Noise-Induced Hearing Loss Animal Model 1-1: Establishing Noise-Induced Hearing Loss Animal Model In order to exclude mice having congenitally abnormal hearing, a preliminary hearing test was performed on all mice before the experiment. A total of 24 7-week-old male Balb/c mice were subjected to an auditory brainstem response (ABR) test and were divided into an experimental group (12 mice) administered with sarpogrelate (50 mg/kg) before exposure to noise and a control group (12 mice) not administered with sarpogrelate.

Figure 1:
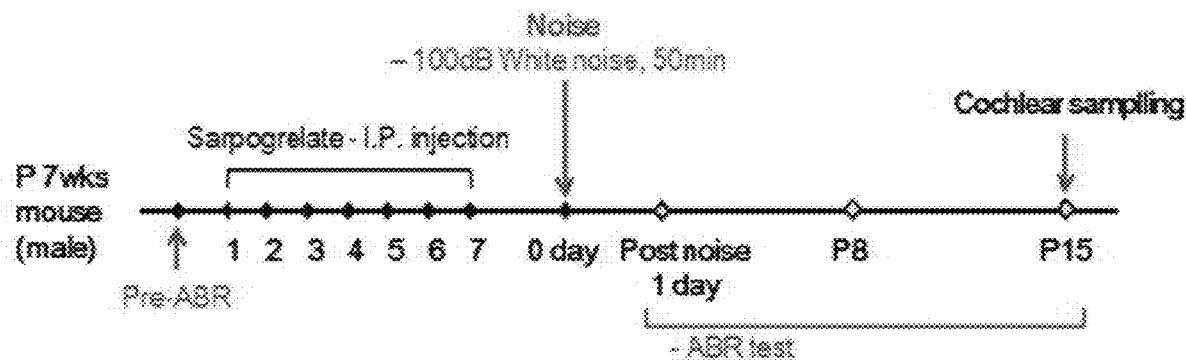
FIG. 1 is a schematic diagram illustrating in-vivo experiments using Balb/c mice.

The sarpogrelate (50 mg/kg) was intraperitoneally administered once a day for 7 days, and the mice were exposed to 100 dB of white noise for 50 minutes after administration, to establish an animal model with noise-induced hearing loss (FIG. 1).

1-2: Hearing Protection by Sarpogrelate 7 days after administration of sarpogrelate (50 mg/kg), an auditory brainstem response (ABR) test was performed to analyze auditory function.

The minimum stimulus sound that forms a wave (V) when applying tone bursts of 8 kHz, 16 kHz and 32 kHz using a Tucker-Davis Technologies (TDT) ABR instrument is determined to be a hearing threshold, the hearing of the experimental group administered with sarpogrelate and the control group not administered with sarpogrelate was measured, and the effect of sarpogrelate on prevention of noise-induced hearing loss was comparatively analyzed.

Figure 2:
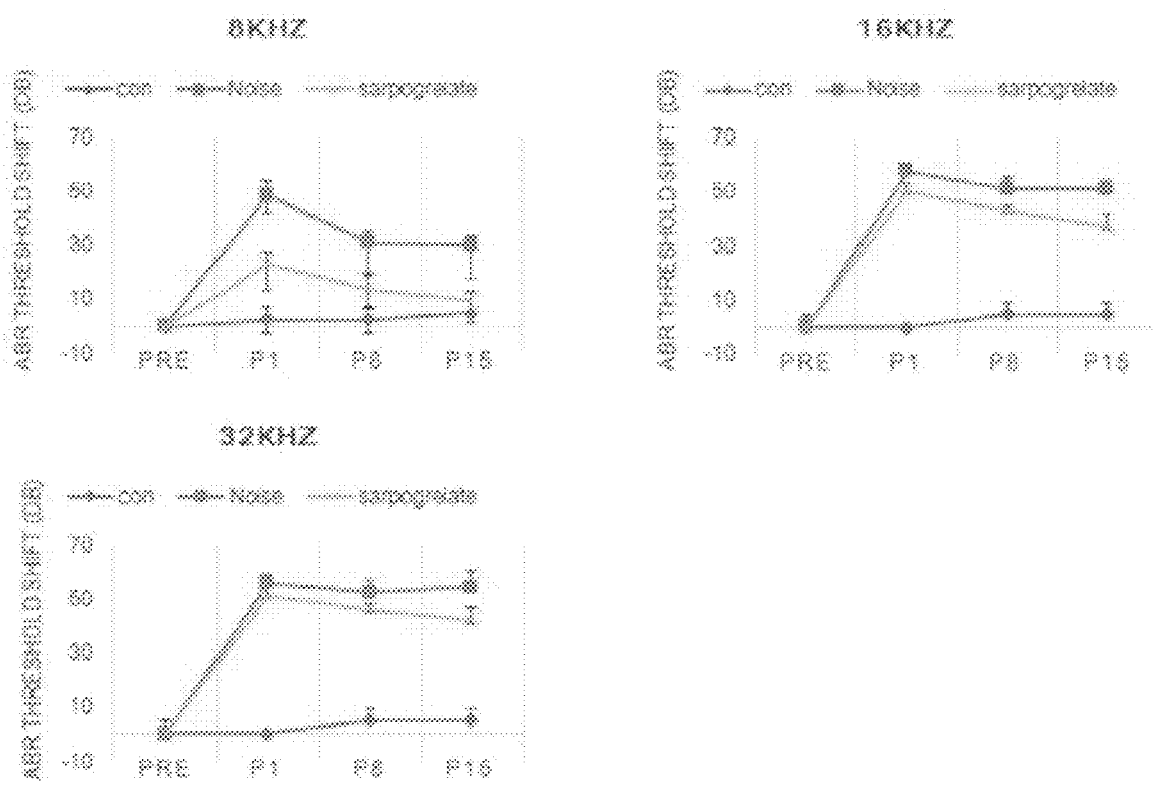
FIG. 2 shows the results of left and right auditory brainstem response (ABR) measured after pretreatment with sarpogrelate and prior to noise exposure, and 1 day, 1 week and 2 weeks after exposure.

As a result, an increase in hearing threshold was observed at 1 day, 7 days and 14 days after exposure to noise. However, the experimental group pre-treated with sarpogrelate was found to have a significantly reduced hearing threshold compared to the control group (FIG. 2). That is, it could be seen that sarpogrelate prevents and protects deterioration in hearing caused by noise.

Example 2

Analysis of Tissue Staining in Noise-Induced Hearing Loss Animal Model

Confocal Laser Scanning Microscopes and immunostaining were performed for the morphological analysis of spiral ganglia and hair cells located in the organ of Corti in the cochlea in noise-induced hearing loss animal model of Example 1.

The expression of anti-oxidation-related proteins was observed in the experimental group pre-treated with sarpogrelate and the control group through tissue immunohistostaining of apex, middle and base helix ganglia and auditory hair cells in the cochlea. The animal tissues were immobilized and embedded with paraffin to obtain tissue sections. Anti-oxidation-related protein antibodies were primarily attached to the tissue sections, fluorescent antibodies were secondarily attached thereto, and immunohistochemistry was performed to analyze the expression behavior of the anti-oxidation-related proteins. The antibodies were subjected to immunohistochemistry with the antioxidant factors, catalase (Abcam, ab1877, Cambridge, UK), SOD2 (Santa Cruz, Calif., USA), and DAPI (Invitrogen, Carlsbad, Calif.).

Figure 3:
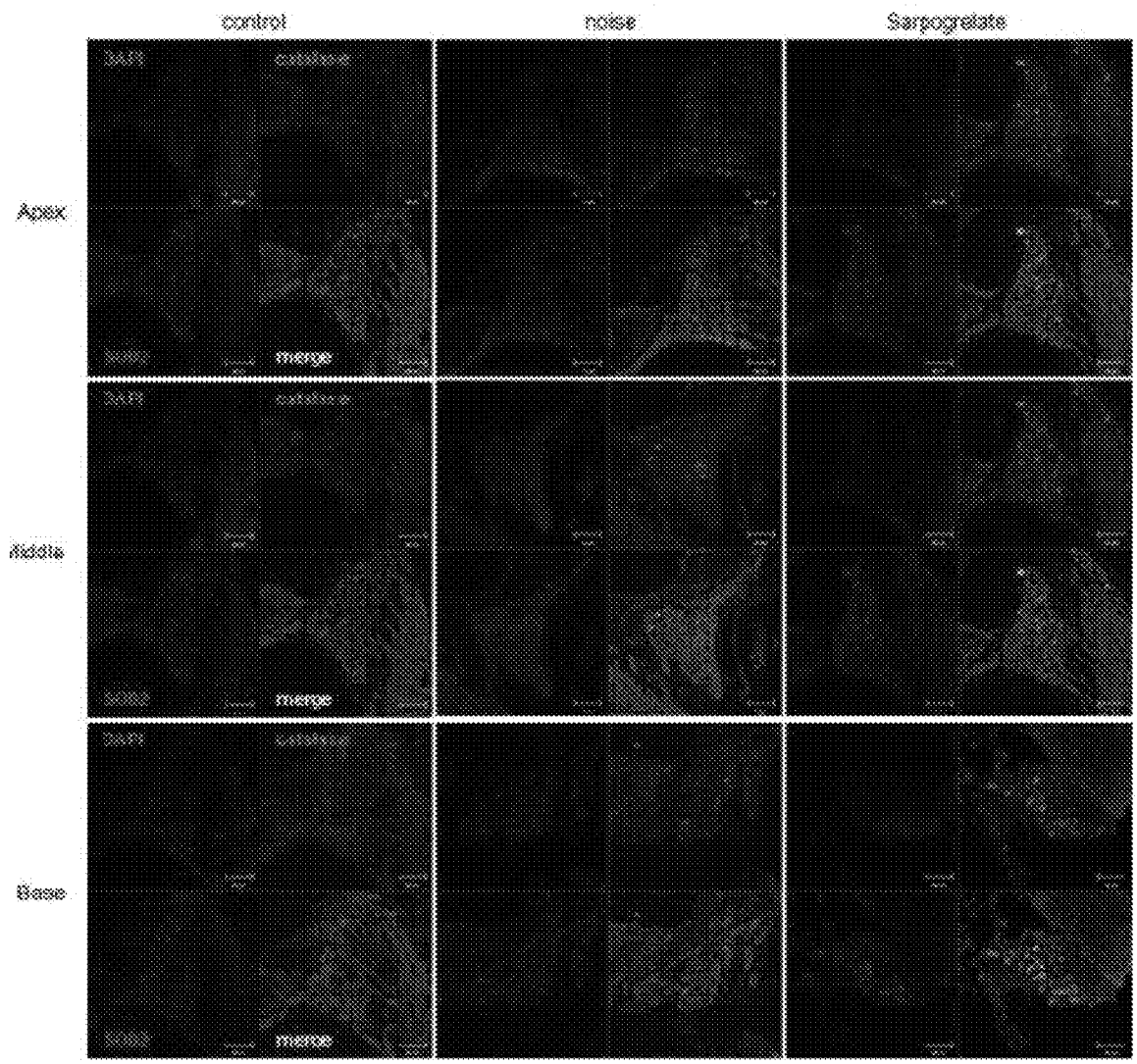
FIG. 3 shows the result of evaluation of the effect of sarpogrelate on the expression of antioxidants (catalase.

As a result, it was found that the expression of catalase and SOD2 as antioxidant enzymes significantly increased in the experimental group pretreated with sarpogrelate (FIGS. 3 and 4). That is, sarpogrelate was found to prevent noise-induced hearing loss.

Example 3

Effect of Sarpogrelate on Inhibition of Apoptosis of Auditory Cell Line

Auditory cell (HEI-OC1; House-Ear Institute-organ of Corti 1) lines expressing auditory genes were used, and the HEI-OC1 cells were cultured at 33° C. and under 10% $CO_2$ in DMEM medium (Dulbecco's modified Eagle's Medium) containing a high concentration of glutamine, supplemented with 10% fetal bovine serum (FBS) and 25 U/ml of interferon gamma.

A noise-induced hearing loss cell line was established through treatment with $H_2O_2$ to produce reactive oxygen species (ROS) by oxidative stress during induction of hearing loss by noise.

After treating with 0.1, 1, 10 and 25 µM sarpogrelate for 24 hours, cytotoxicity of sarpogrelate was measured through WST-1 analysis. In addition, after pretreatment with 0.1, 1, 10 and 25 µM sarpogrelate for 1 hour and treatment with 500 µM $H_2O_2$ for 24 hours, the effects of sarpogrelate on cytotoxicity and apoptosis caused by $H_2O_2$ were quantitatively evaluated through WST-1 analysis (Takara-Bio, Tokyo, Japan).

As a result, sarpogrelate was found not to cause cytotoxicity, and had an effect of inhibiting apoptosis of auditory cells caused by $H_2O_2$ (FIG. 5).

Example 4

Anti-Oxidative Effect in Auditory Cells by Sarpogrelate

The antioxidative activity of sarpogrelate was analyzed in the noise-induced hearing loss cell line by treatment with $H_2O_2$ of Example 3.

The cell line was pre-treated with sarpogrelate at 1, 10, 25 and 50 µM for 1 hour and treated with 250 µM $H_2O_2$ for 24 hours, and mRNA and protein expression of the antioxidant enzymes, catalase and SOD2 (superoxide dismutase 2) was observed. The mRNA expression was determined by quantitative real-time PCR after extraction of total RNA and synthesis of cDNA. Protein expression was observed by extracting total protein with RIPA buffer, separating proteins in the order of size by SDS-PAGE and then attaching catalase (catalase, Abcam, ab1877, Cambridge, UK)) and SOD2 (superoxide dismutase 2, Santa Cruz, Calif., USA) thereto.

As a result, it was found that the expression of mRNA and proteins of catalase and SOD2 was increased in the experimental group treated with sarpogrelate (FIGS. 6 and 7). That is, in-vitro results using auditory cell lines also showed that sarpogrelate protects hearing, as shown by the result of the noise-induced hearing loss animal experiment.

In addition, sarpogrelate can exert a synergetic effect on the treatment of sensorineural hearing loss through co-administration of sarpogrelate with Korean red ginseng extract, *Ginkgo biloba* extract, resveratrol, *Vitis vinifera* dry leaf extract, montelukast and the like, that is, co-administration of a complex preparation containing a composition for treating sensorineural hearing loss containing sarpogrelate or a pharmaceutically acceptable salt thereof as an active ingredient and at least one selected from the group consisting of a Korean red ginseng extract, a *Ginkgo biloba* extract, resveratrol, a *Vitis vinifera* dry leaf extract and montelukast as an active ingredient.

INDUSTRIAL APPLICABILITY

The composition containing sarpogrelate according to the present invention protects noise-induced hearing loss through inhibition of apoptosis of auditory cells and increased expression of antioxidant enzymes in the auditory cells, thus being useful for preventing and alleviating sensorineural hearing loss.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

The invention claimed is:

1. A method of preventing or treating sensorineural hearing loss, the method comprising:
    administering sarpogrelate or a pharmaceutically acceptable salt thereof.

2. The method of claim 1, further comprising administering at least one selected from the group consisting of a Korean red ginseng extract, a *Ginkgo biloba* extract, resveratrol, and a European *Vitis vinifera* dry leaf extract.

3. The method of claim 1, wherein the sensorineural hearing loss is noise-induced hearing loss, ototoxic hearing loss, sudden hearing loss or age-related hearing loss.

4. The method of claim 1, wherein the sensorineural hearing loss is caused by damage to inner ear hair cells and surrounding tissues.

5. The method of claim 1, wherein said sarpogrelate or pharmaceutically acceptable salt thereof is administered in a composition, and the composition inhibits apoptosis of auditory cells and increases expression of antioxidant enzymes in the auditory cells.

6. The method of claim 1, wherein the pharmaceutically acceptable salt comprises at least one salt selected from the group consisting of hydrochloride, sulfate, mesylate, malate, maleate, besylate, hydrogen sulfate, oxalate, fumarate, tartrate, citrate, succinate, acetate and phosphate.

7. A method of preventing or treating sensorineural hearing loss, the method comprising:
    administering a complex preparation containing sarpogrelate or a pharmaceutically acceptable salt thereof, and at least one selected from the group consisting of a Korean red ginseng extract, a Ginkgo biloba extract, resveratrol, and a European Vitis vinifera dry leaf extract.

8. The method of claim 7, wherein the complex preparation is a tablet, an effervescent tablet, a granule, a powder, an injection, a pill or a capsule.

9. A method of preventing or treating sensorineural hearing loss, the method comprising:
    co-administering sarpogrelate or a pharmaceutically acceptable salt thereof with at least one selected from the group consisting of a Korean red ginseng extract, a Ginkgo biloba extract, resveratrol, and a European Vitis vinifera dry leaf extract.

10. The method of claim 9, wherein the co-administration is carried out sequentially or simultaneously.

* * * * *